US00PP35644P2

(12) United States Plant Patent
Bean et al.

(10) Patent No.: US PP35,644 P2
(45) Date of Patent: Feb. 6, 2024

(54) ***AGAPANTHUS* PLANT NAMED 'DWAGHYB01'**

(50) Latin Name: ***Agapanthus* hybrid**
Varietal Denomination: DWAgHyb01

(71) Applicant: De Wet Plant Breeders, Johannesburg (ZA)

(72) Inventors: Quinton Bean, Northriding (ZA); Charles Andrew De Wet, Sandton (ZA)

(73) Assignee: DE WET PLANT BREEDERS, Johannesburg (ZA)

( * ) Notice: Subject to any disclaimer, the term of this patent is extended or adjusted under 35 U.S.C. 154(b) by 0 days.

(21) Appl. No.: 18/112,983

(22) Filed: Feb. 22, 2023

(30) Foreign Application Priority Data

Sep. 23, 2022 (QZ) ..... PBR 20222143

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
CPC ..... A01H 5/02; A01H 5/00; A01H 6/04
See application file for complete search history.

(56) References Cited

U.S. PATENT DOCUMENTS

PP30,164 P2 * 1/2019 Bean ..... A01H 5/02
Plt./398

OTHER PUBLICATIONS

Concept Plants *Agapanthus* Blue Thunder, retrieved on Jun. 7, 2023 at https://conceptplants.com/varieties/agapanthus-blue-thunder-sdb002, 2 pp. (Year: 2023).*

* cited by examiner

*Primary Examiner* — June Hwu
(74) *Attorney, Agent, or Firm* — Penny J. Aguirre

(57) ABSTRACT

A new cultivar of *Agapanthus* plant named 'DWAgHyb01' that is characterized by its long flowering period with good re-blooming, its high quantity of flowers per umbel that are vividly dark blue in color, its good resistance to root and crown rot, and its medium plant height (70 to 80 cm).

2 Drawing Sheets

Botanical classification: *Agapanthus* hybrid.
Varietal denomination: 'DWAgHyb01'.

CROSS REFERENCE TO RELATED APPLICATIONS

This application claims priority to European Community Plant Variety Office (CPVO) Plant Breeder's Rights Application No. 2022/2143 filed Sep. 23, 2022. The Applicant received the information for the Plant breeders' rights application directly from the Inventor. This application is also co-pending with a U.S. Plant Patent Application filed for a plant derived from the same breeding program that is entitled *Agapanthus* Plant Named 'DWAgHyb02' (U.S. Plant patent application Ser. No. 18/112,907).

BACKGROUND OF THE INVENTION

The present invention relates to a new and distinct cultivar of *Agapanthus* of hybrid origin and will be referred to hereafter by its cultivar name, 'DWAgHyb01'. 'DWAgHyb01' represents a new perennial grown for landscape and container use.

The new cultivar was derived from a controlled breeding program by the Inventors in Hartebeespoort, North West Province, South Africa. The goal of the breeding program was to develop a new cultivar of *Agapanthus* with large sized inflorescences that are dark blue in color, resistance to crown rot, and a reblooming habit. The Inventor made a cross in October of 2015 between unnamed proprietary plants of *Agapanthus* from the Inventors' breeding program as both the female and male parents. The Inventors selected 'DWAgHyb01' in November of 2017 as a single unique plant amongst the seedlings that resulted from the above cross.

Asexual propagation of the new cultivar was first accomplished by division by one of the Inventors in Hartebeespoort, North West Province, South Africa in October of 2017. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'DWAgHyb01' as a distinct cultivar of *Agapanthus*.

1. 'DWAgHyb01' exhibits a long flowering period with good re-blooming.
2. 'DWAgHyb01' exhibits a high quantity of flowers per umbel that are vividly dark blue in color.

3. 'DWAgHyb01' exhibits good resistance to root and crown rot.
4. 'DWAgHyb01' exhibits a medium plant height (70 to 80 cm).

The female parent of 'DWAgHyb01' differs from 'DWAgHyb01' in having flowers that are lighter in color and in having a slower growth habit. The male parent of 'DWAgHyb01' differs from 'DWAgHyb01' in having flowers that are lighter in color and in having a faster growth habit. 'DWAgHyb01' can be most closely compared to the *Agapanthus* cultivars 'Black Pantha' (not patented), 'Sbd002' (U.S. Plant Pat. No. 30,164 P2) and 'DWAgHyb02'. 'Black Pantha' is similar to 'DWAgHyb01' in having flowers that are blue in color. 'Black Pantha' differs from 'DWAgHyb01' in having flowers that are lighter blue and less uniform in color with more purple tones on the inside of the tepals, a less vigorous growth habit, and in lacking a re-blooming habit. 'Sbd002' is similar to 'DWAgHyb01' in having a high quantity of flowers per umbel that are blue in color. 'Sbd002' differs from 'DWAgHyb01' in having flowers that are lighter blue in color, inflorescences that are smaller in size and foliage that is less grey in color. 'DWAgHyb02' differs from 'DWAgHyb01' in having flowers that are more purple in color, a slightly more compact plant habit, a more vigorous growth habit, and less reblooming.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Planttipp, Crocus, De Witt Plant Breeders (youtube), Thompson and Morgan, Peter van Rijssen (linkedin), Perfect Garden, Hoogeveen Plants, Fairweather' s Nursery, Plant Lust, Bali-Hai Nursery (ebay), Oz Planten, Plant Estate, Spijker and Lichtnelke.

BRIEF DESCRIPTION OF THE DRAWINGS

The accompanying color photographs illustrate the overall appearance and distinct characteristics of the new *Agapanthus*. The photographs were taken of plants 2 years in age of 'DWAgHyb01' as grown outdoors in a 30-cm container in Linbro Park, Johannesburg, South Africa.

The photograph in FIG. 1 provides a side view of a plant of 'DWAgHyb01' in bloom.

Figure 1:
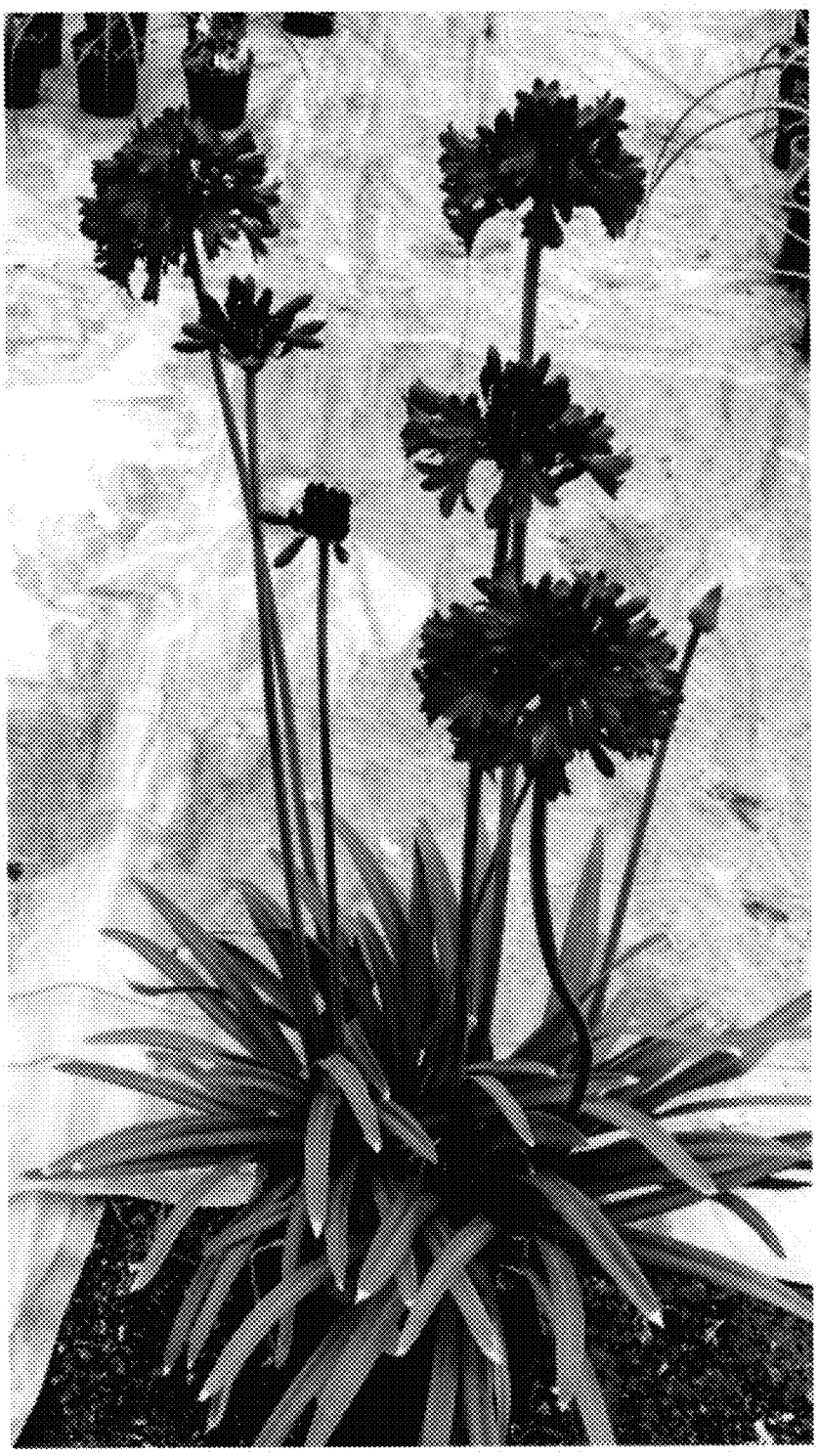
Figure 2:
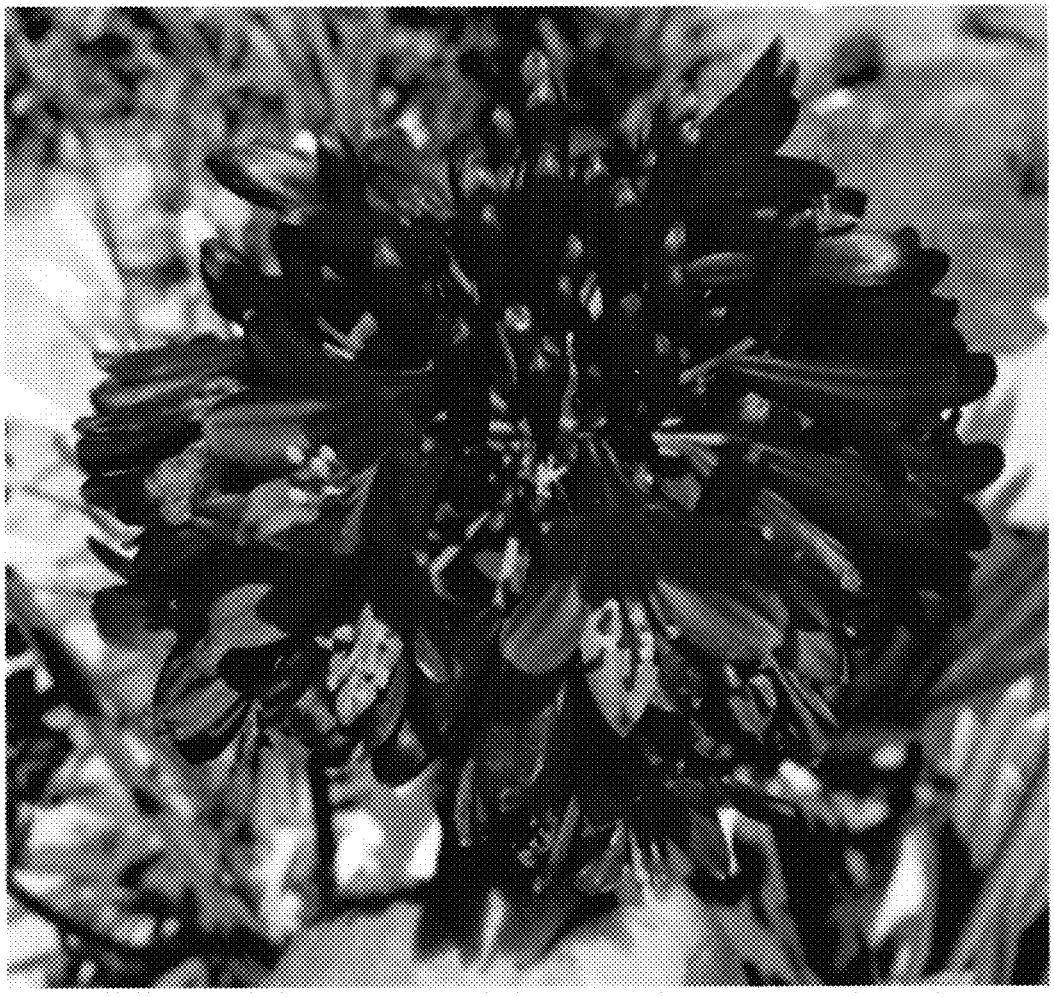

The photograph in FIG. 2 provides a close-up view of an inflorescence of 'DWAgHyb01'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 2-year-old plants of 'DWAgHyb01' as grown outdoors in 15-cm containers in Waddinxveen, The Netherlands. The phenotype of the new cultivar may vary with variations in environmental, climatic, and cultural conditions, as it has not been tested under all possible environmental conditions. The color determinations are in accordance with the 2015 Colour Chart of The Royal Horticultural Society, London, England, except where general color terms of ordinary dictionary significance are used.

General description:

*Blooming period.*—Main blooming period; early to mid-summer with re-blooms sporadically through the year in South Africa.

*Plant type.*—Semi-deciduous (climate dependent) herbaceous perennial.

*Plant habit.*—Basal rosettes with inflorescences emerging from the rosette center.

*Height and spread.*—65 cm in height and 50 cm in spread as a 2-year-old plant, reaches 70 to 80 cm in height as grown in the landscape.

*Cold hardiness.*—At least to U.S.D.A. Zone 8.

*Diseases and pests.*—Good resistance has been observed to crown rot caused by *Fusarium* sp. and root rot caused by *Erwinia* sp., no resistance or susceptibility to pests has been observed.

*Root description.*—Thick and fleshy.

*Propagation.*—Division and Tissue culture (preferred).

*Growth rate.*—Vigorous.

*Number of shoots* (*rosettes*).—An average of 2.

Foliage description:

*Leaf shape.*—Ligulate.

*Leaf division.*—Simple.

*Leaf base.*—Truncate.

*Leaf arrangement.*—2-ranked, arranged in shoots an average of 3.5 cm diameter at base.

*Leaf apex.*—Narrow acute.

*Leaf aspect.*—Emerging leaves erect, then cascade.

*Leaf venation.*—Parallel, upper surface; matches surface color, mid-rib between 144B and 144C, lower surface; matches surface color, mid-rib 144A.

*Leaf margins.*—Entire.

*Leaf size.*—Up to 32 cm in length and up to 3 cm in width.

*Leaf surface.*—Smooth, glabrous, and dull on upper and lower surface.

*Leaf number.*—Average of 8 leaves per rosette.

*Foliage density.*—Medium.

*Leaf color.*—Young leaves upper surface; 144A, top 138A, young leaves lower surface; 144A and 144B, mature leaves upper surface; 137A, base 137B (no anthocyanin present), mature leaves lower surface; 137B, base anthocyanin present N92A and 86A in color.

*Leaf attachment.*—Sessile to base.

Flower description:

*Inflorescence type.*—Dense umbel.

*Flower fragrance.*—None.

*Flower type.*—Rotate, campanulate, base of tepals fused.

*Flower number.*—An average of 50 flowers per umbel.

*Inflorescence size.*—Average of 10 cm in height, 13 cm in diameter.

*Flower size.*—An average of 4 cm in depth and 3.3 cm in diameter.

*Lastingness of inflorescence.*—Average 7 days.

*Flower aspect.*—Primarily upright.

*Peduncle.*—1 per rosette, very strong, oval in shape, held primarily upright, surface is satiny, glabrous, slightly glaucous, average of 55 cm in length and 1.2 cm in width at distal region and 1.8 cm in width at proximal region, color; young 144A, mature 137A, top 137B, no anthocyanin present.

*Pedicels.*—Very strong, average of 3.5 cm in length and 2 mm in width, held erect to outward, color; 138A, top mottled with N89A, glabrous surface.

*Flower buds.*—Obelliptic in shape, glabrous surface, average of 2.3 cm in length and 9 mm in width, color; N92C, before burst N92C faintly flushed with N92B and N89A.

*Tepals* (*perianth*).—6 lobes rotate, oblanceolate in shape, lower 25% fused, entire margins, apex is rounded to acute, inner tepals rounded with a slight notch, glabrous and satiny on inner and outer surfaces, thick substance, an average of 2.8 cm in length and 1.2 cm in width, color; outer surface N89A, center and margins between N92B and N92C, inner surface N155A, base N89C, center and margins N89A.

*Bracts.*—Ovate to lanceolate in shape, acuminate apex, truncate base, glabrous and matte surface, 3.2 cm in length, 2 cm in width, color; 144A, veins 138A, base 145B.

Reproductive organs:

*Gynoecium.*—Pistil; 1, average of 2.2 cm in length, stigma; narrow clavate in shape, N89D in color, style; 2.1 cm in length, N155A, top N89D, ovary; oblong in shape, 1 cm in length, 4 mm in width and 145C in color, pistillodes not present.

*Androecium.*—Stamens; 6, anthers; dorsifixed, extrusion absent to weak, obcordate in shape, average of 2 mm in length, 202A in color, filament; 2.2 cm in length, color; N155A, top N89D, pollen; abundant in quantity and 135B in color, staminodes not present.

*Fruit/Seed.*—None observed.

It is claimed:

1. A new and distinct cultivar of *Agapanthus* plant named 'DWAgHyb01' as herein illustrated and described.

* * * * *